(12) United States Patent
Tsai et al.

(10) Patent No.: US 10,064,737 B2
(45) Date of Patent: Sep. 4, 2018

(54) IMPLANT DEVICE FOR OSSEOUS INTEGRATION

(71) Applicant: INDUSTRIAL TECHNOLOGY RESEARCH INSTITUTE, Hsinchu (TW)

(72) Inventors: Jane S C Tsai, Taipei (TW); Hsin-Hsin Shen, Zhudong Township, Hsinchu County (TW); Fang-Hei Tsau, Kaohsiung (TW); Ji-Bin Horng, Tainan (TW); Pei-I Tsai, Hsinchu (TW); Chih-Chieh Huang, Zhunan Township, Miaoli County (TW); Yi-Hung Wen, Hsinchu (TW); Hong-Jen Lai, Hsinchu (TW); Sung-Ho Liu, Kaohsiung (TW); Ching-Chih Lin, Tainan (TW); Meng-Huang Wu, Taipei (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 294 days.

(21) Appl. No.: 14/977,234

(22) Filed: Dec. 21, 2015

(65) Prior Publication Data

US 2017/0156878 A1 Jun. 8, 2017

(30) Foreign Application Priority Data

Dec. 7, 2015 (TW) .............................. 104140981 A (51) Int. Cl.
*A61F 2/44* (2006.01)
*A61B 17/86* (2006.01)

(52) U.S. Cl.
CPC .............. *A61F 2/442* (2013.01); *A61B 17/86* (2013.01); *A61F 2/447* (2013.01); *A61F 2/4455* (2013.01); *A61F 2002/4475* (2013.01)

(58) Field of Classification Search
CPC ..................................................... A61F 2/4455
See application file for complete search history.

(56) References Cited

U.S. PATENT DOCUMENTS 5,116,337 A  5/1992 Johnson
5,282,861 A  2/1994 Kaplan
(Continued)

FOREIGN PATENT DOCUMENTS

CN  1088423 A  6/1994
CN  1098281 A  2/1995
(Continued)

OTHER PUBLICATIONS

Chinese Office Action and Search Report issued in Chinese Application No. 201410406040.6 dated Jan. 17, 2017.
(Continued)

*Primary Examiner* — Andrew Yang
(74) *Attorney, Agent, or Firm* — Birch, Stewart, Kolasch & Birch, LLP (57) ABSTRACT

An implant device for osseous integration includes a plurality of connection bars and at least one frame bar. These connection bars are connected with each other to form a three-dimensional (3D) grid structure. The frame bar is connected with at least two of the connection bars to define at least one edge of the 3D grid structure. Wherein, the frame bar has a diameter substantially greater than that of these connection bars.

19 Claims, 7 Drawing Sheets

(56) References Cited

U.S. PATENT DOCUMENTS

| | | |
|---|---|---|
| 5,876,434 A | 3/1999 | Flomenblit et al. |
| 6,063,442 A | 5/2000 | Cohen et al. |
| 7,322,983 B2 | 1/2008 | Harris |
| 7,799,079 B2 | 9/2010 | Hestad et al. |
| 7,892,267 B2 | 2/2011 | Lancial et al. |
| 8,034,111 B2 | 10/2011 | Hsu et al. |
| 8,128,700 B2 | 3/2012 | Delurio et al. |
| 8,142,484 B2 | 3/2012 | Chao et al. |
| 8,303,879 B2 | 11/2012 | Bertele et al. |
| 8,361,150 B2 | 1/2013 | Zhang et al. |
| 8,414,650 B2 | 4/2013 | Bertele et al. |
| 8,470,042 B2 | 6/2013 | Zhang et al. |
| 8,535,357 B2 | 9/2013 | Stone et al. |
| 8,556,949 B2 | 10/2013 | Teisen et al. |
| 8,628,582 B2 | 1/2014 | Lavi |
| 8,632,592 B2 | 1/2014 | Barrall |
| 8,685,101 B2 | 4/2014 | Kraft et al. |
| 9,060,873 B2 | 6/2015 | Abdou |
| 9,155,578 B2 | 10/2015 | Chegini et al. |
| 2002/0198527 A1 | 12/2002 | Muckter |
| 2004/0122431 A1 | 6/2004 | Biedermann et al. |
| 2004/0162560 A1 | 8/2004 | Raynor et al. |
| 2004/0210217 A1 | 10/2004 | Baynham et al. |
| 2005/0143823 A1 | 6/2005 | Boyd et al. |
| 2005/0192675 A1 | 9/2005 | Robinson |
| 2006/0100630 A1 | 5/2006 | West, Jr. |
| 2007/0038221 A1 | 2/2007 | Fine et al. |
| 2007/0141110 A1 | 6/2007 | Stone et al. |
| 2008/0107890 A1 | 5/2008 | Bureau et al. |
| 2009/0240289 A1 | 9/2009 | Zipprich et al. |
| 2010/0042215 A1 | 2/2010 | Stalcup et al. |
| 2010/0082067 A1 | 4/2010 | Kondrashov |
| 2010/0262244 A1 | 10/2010 | Savage-Erickson et al. |
| 2010/0304065 A1 | 12/2010 | Tomantschger et al. |
| 2011/0071636 A1 | 3/2011 | Tsuang et al. |
| 2011/0213423 A1 | 9/2011 | Biedermann et al. |
| 2011/0307073 A1 | 12/2011 | Teoh et al. |
| 2012/0083882 A1 | 4/2012 | Shih et al. |
| 2012/0184993 A1 | 7/2012 | Arambula et al. |
| 2012/0271362 A1 | 10/2012 | Martineau et al. |
| 2013/0030529 A1* | 1/2013 | Hunt .................. A61F 2/30771 623/16.11 |
| 2013/0123862 A1 | 5/2013 | Anderson et al. |
| 2013/0166028 A1 | 6/2013 | Shieh et al. |
| 2013/0325129 A1 | 12/2013 | Huang |
| 2015/0018956 A1 | 1/2015 | Steinmann et al. |
| 2015/0093717 A1 | 4/2015 | Ali |
| 2015/0112342 A1 | 4/2015 | Penzimer et al. |
| 2016/0026049 A1 | 1/2016 | Park et al. |

FOREIGN PATENT DOCUMENTS

| | | |
|---|---|---|
| CN | 1204498 A | 1/1999 |
| CN | 2894638 Y | 5/2007 |
| CN | 101128166 A | 2/2008 |
| CN | 101198291 A | 6/2008 |
| CN | 201082188 Y | 7/2008 |
| CN | 101317790 A | 12/2008 |
| CN | 201840550 U | 5/2011 |
| CN | 102574362 A | 7/2012 |
| CN | 202682036 U | 1/2013 |
| CN | 103167837 A | 6/2013 |
| CN | 206167016 U | 5/2017 |
| EP | 1 112 722 A2 | 7/2001 |
| EP | 1 069 872 B1 | 5/2003 |
| EP | 1 762 189 A1 | 3/2007 |
| EP | 2 400 901 B1 | 5/2013 |
| EP | 2 531 147 B1 | 7/2015 |
| EP | 2 477 578 B1 | 8/2015 |
| TW | 480169 A | 3/2002 |
| TW | 200416020 A | 9/2004 |
| TW | 200635565 A | 10/2006 |
| TW | 200708295 A | 3/2007 |
| TW | 200722036 A | 6/2007 |
| TW | M333885 U | 6/2008 |
| TW | 200936113 A | 9/2009 |
| TW | 200944176 A1 | 11/2009 |
| TW | 201221108 A1 | 6/2012 |
| TW | 201235005 A1 | 9/2012 |
| TW | M438893 U1 | 10/2012 |
| TW | 201249392 A1 | 12/2012 |
| TW | 201325545 A1 | 7/2013 |
| TW | 201325577 A1 | 7/2013 |
| TW | 201325638 A1 | 7/2013 |
| TW | M474521 U | 3/2014 |
| TW | 201519854 A | 6/2015 |
| WO | WO 2011/059995 A2 | 5/2011 |
| WO | WO 2012/024665 A2 | 2/2012 |
| WO | WO 2013/043218 A1 | 3/2013 |
| WO | WO 2013/043432 A1 | 3/2013 |

OTHER PUBLICATIONS

Taiwanese Office Action and Search Report issued in Taiwanese Application No. 104140981 dated Feb. 18, 2017.

U.S. Office Action issued in U.S. Appl. No. 14/555,204 dated Jan. 12, 2017.

U.S. Office Action for U.S. Appl. No. 14/554,521, dated Sep. 7, 2017.

U.S. Office Action for U.S. Appl. No. 14/585,894, dated Sep. 21, 2017.

Beng, "Selective Laser Sintering of a Stainless Steel Powder," University of Leeds School of Mechanical Engineering, Leeds UK, Doctor of Philosophy (Dissertation), Jul. 2003, pp. 1-279 (Total 310 pages).

Cheng et al., "Additively Manufactured 3D Porous Ti-6Al-4V Constructs Mimic Trabecular Bone Structure and Regulate Osteoblast Proliferation, Differentiation and Local Factor Production in a Porosity and Surface Roughness Dependent Manner," Biofabrication, vol. 6, Oct. 7, 2014, 13 pages.

Kang et al., "Porous Biodegradable Lumbar Interbody Fusion Cage Design and Fabrication Using Integrated Global-Local Topology Optimization With Laser Sintering," Journal of Biomechanical Engineering, vol. 135, Oct. 2013, pp. 101013-1-101013-8.

Lin et al., "Structural and Mechanical Evaluations of a Topology Optimized Titanium Interbody Fusion Cage Fabricated by Selective Laser Melting Process," Wiley InterScience, Published online Apr. 5, 2007, pp. 272-279.

Murr et al., "Metal Fabrication by Additive Manufacturing Using Laser and Electron Beam Melting Technologies," J. Mater. Sci, Technol., vol. 28, No. 1, 2012, pp. 1-14.

Pauly et al., "Processing Metallic Glasses by Selective Laser Melting," Materials Today, vol. 16, Nos. 1/2, Jan./Feb. 2013, pp. 37-41.

Wieding et al., "Numerical Optimization of Open-porous Bone Scaffold Structures to Match the Elastic Properties of Human Cortical Bone," Journal of the Mechanical Behavior of Biomedical Materials, vol. 37, 2014 (Available online May 14, 2014), pp. 56-68.

Yang et al., "Laser Solid Forming Zr-based Bulk Metallic Glass," Intermetallics, vol. 22, 2012 (Available online Nov. 27, 2011), pp. 110-115.

Yavari et al., "Fatigue Behavior of Porous Biomaterials Manufactured Using Selective Laser Melting," Materials Science and Engineering C, vol. 33, 2013 (Available online Aug. 13, 2013), pp. 4849-4858.

Zhang et al., "Microstructural Analysis of $Zr_{55}Cu_{30}Al_{10}Ni_5$ Bulk Metallic Glasses by Laser Surface Remelting and Laser Solid Forming," Intermetallics, vol. 66, 2015 (Available online Jun. 25, 2015), pp. 22-30.

U.S. Office Action for U.S. Appl. No. 14/555,251, dated Dec. 4, 2017.

U.S. Office Action for U.S. Appl. No. 14/585,894, dated Jan. 31, 2018.

Taiwanese Office Action and Search Report for Taiwanese Application No. 106128720, dated Jun. 1, 2018.

(56) References Cited

OTHER PUBLICATIONS

US Office Action for U.S. Appl. No. 14/555,251, dated May 25, 2018.

* cited by examiner

IMPLANT DEVICE FOR OSSEOUS INTEGRATION

This application claims the benefit of Taiwan application Serial No. 104140981, filed Dec. 7, 2015, the disclosure of which is incorporated by reference herein in its entirety.

TECHNICAL FIELD

The technical field relates in general to a biocompatible implant device and an implant device for osseous integration.

BACKGROUND

Ideal medical material should be capable of being tightly bonded with tissues and applicable to complicated structure to strengthen the critical design of specific parts. However, most of existing implantable medical products are formed of one single material. To take the orthopedic products, such as bone screws, spinal fixation device, inter-body fusion device, artificial disk, and artificial joints that are implanted into bone tissues, for example, most of the orthopedic products are formed of one single material, such as a metal or a biomedical polymer material.

In respect of the applicableness of the material and the compatibility between the material and human bone tissues, although metal material has excellent strength of support and osseo-integration, stress shielding effect may still occurs at normal bone tissue interface due to the huge difference in the elastic modulus between bone tissues and metal material and cause bone tissue structure to collapse. Biomedical polymer material that is characterized as a bio-inert and hydrophobic material lacking the function of inducing bone cells to grow and attach thereon cannot be easily fused with bone cells and has the risk of pull out the bone tissues, despite having an elastic modulus similar to human bone tissues and being capable of reducing the stress shielding effect through suitable distribution of stress to avoid the collapse and loss of bone tissues. Currently, composite material composed of metal and biomedical polymer is applied to produce implant devices for osseous integration to get the benefits respectively provide by the metal material and the biomedical polymer material.

However, since the implant devices for osseous integration composed by the metal/biomedical polymer based composite material still do not have enough bonding strength for resisting the sudden impact resulted from the surgical operation or the prolonged extrusion stress provided by the peripheral cartilage or bone tissues, thus delamination of the implanted device may occur and the components of the implanted device may shift to unwanted location.

Therefore, it is necessary to provide an advanced osseous integration implant device.

SUMMARY

According to one embodiment of the present disclosure, an implant device for osseous integration is provided, wherein the implant device for osseous integration includes a plurality of connection bars and at least one frame bar. These connection bars are connected with each other to form a three-dimensional (3D) grid structure. The frame bar is connected with at least two of the connection bars to define at least one edge of the 3D grid structure. Wherein, the frame bar has a diameter substantially greater than that of these connection bars.

According to another embodiment, the implant device for osseous integration further includes a polymer body contained within the 3D grid structure to form a frictional interface having a contact area directly in contact with the 3D grid structure. Wherein the ratio of the contact area to an overlapping area formed between the 3D grid structure and the polymer body substantially ranges from 3% to 5%.

According to yet another embodiment, the implant device for osseous integration further includes a polymer body connected to the 3D grid structure through a metal interface layer having a connecting area directly in contact with the 3D grid structure. Wherein the ratio of the connecting area to an overlapping area formed between the metal interface layer and the 3D grid structure substantially ranges from 3% to 5%.

According to the aforementioned embodiments, an implant device for osseous integration is disclosed. The implant device for osseous integration includes a plurality of connection bars used for forming a 3D grid structure and at least one frame bar used to define at least one edge of the 3D grid structure. Because the frame bar has a diameter substantially greater than that of these connection bars can provide the 3D grid structure more rigid structure for resisting the sudden impact resulted from the surgical operation or the prolonged extrusion stress provided by the peripheral cartilage or bone tissues, so as to avoid delamination and unwanted shift occurring on the implanted device.

BRIEF DESCRIPTION OF THE DRAWINGS

The above objects and advantages of the present disclosure will become more readily apparent to those ordinarily skilled in the art after reviewing the following detailed description and accompanying drawings, in which.

DETAILED DESCRIPTION

The present specification discloses an implant device for osseous integration to solve the problems of delamination and unwanted shift occurring on the implanted device due to the sudden impact resulted from the surgical operation or the prolonged extrusion stress provided by the peripheral cartilage or bone tissues. To make the above purposes, features and advantages of the disclosure easy to understand, a number of exemplary embodiments with accompanying drawings are disclosed below with detailed descriptions.

However, it should be noted that these embodiments are not for limiting the invention. The invention can also be implemented by using other technical features, elements, methods and parameters. A number of exemplary embodiments are disclosed for illustrating technical features of the invention, not for limiting the claims of the invention. Anyone who is skilled in the technology field of the invention can make necessary modifications or variations to the structures according to the needs in actual implementations. In different drawings and embodiments, the same elements are represented by the same designations.

Figure 1A:
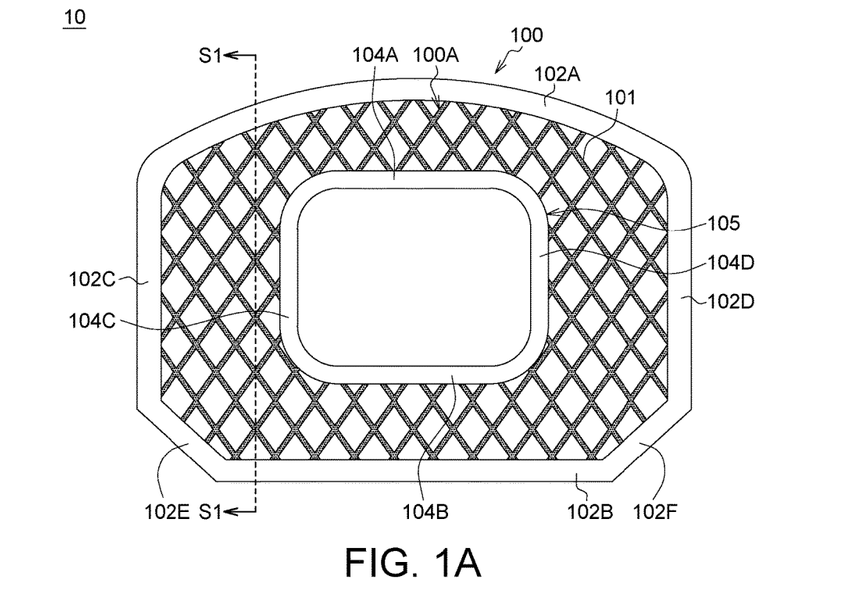
FIG. 1A is a top view illustrating an implant device for osseous integration in accordance with one embodiment of the present disclosure.
Figure 1B:
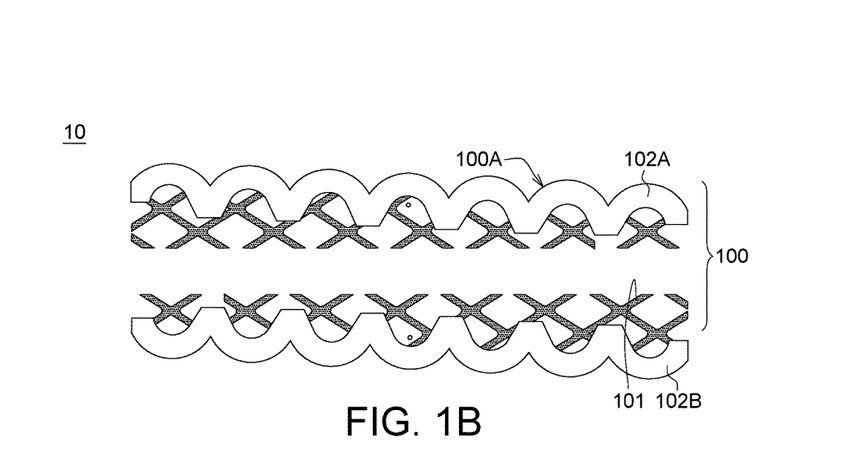
FIG. 1B is a cross-sectional view of the implant device for osseous integration taken along the section line S1 depicted in FIG. 1A.

FIG. 1A is a top view illustrating an implant device 10 for osseous integration in accordance with one embodiment of the present disclosure; and FIG. 1B is a cross-sectional view of the implant device for osseous integration taken along the section line S1 depicted in FIG. 1A. The implant device 10 includes a plurality of connection bars 101 and at least one frame bar. These connection bars 101 are connected with each other to form a 3D grid structure 100. The frame bar is connected with at least two of the connection bars 101 to define at least one edge of the 3D grid structure. Wherein, the frame bar has a diameter substantially greater than that of these connection bars.

For example, in some embodiments of the present disclosure, the implant device 10 includes a plurality of frame bars connecting with each other to define a 3D frame structure (not shown) and a plurality of connection bars 10 connecting with each other by using the 3D frame structure as the skeleton (framework) to form a 3D grid structure 100. However, the physical structure of the implant device 10 is not limited as to this regard.

In another embodiment of the present disclosure, the implant device 10 includes a single oval-shaped, circular or irregular ring-shaped frame bar (not shown) serving as an edge to define a flat face of a 3D grid structure 100 that is formed by a plurality of connection bars 101 connected with each other.

In the present embodiment, the implant device 10 includes a plurality of connection bars 101, an arc frame bar 102A and five straight frame bars 102B, 102C, 102D, 102E and 102F. The connection bars 101 connect with each other to form a 3D grid structure 100. The arc frame bar 102A and the five straight frame bars 102B, 102C, 102D, 102E and 102F connect with each other to form a hexagon frame, and each of which connects with at least two of these connection bars 101 extending along different directions (e.g. two directions perpendicular with each other), so as to define a top flat face 100A of the 3D grid structure 100.

Wherein, each of the arc frame bar 102A and the five straight frame bars 102B, 102C, 102D, 102E and 102F has a diameter substantially greater than that of these connection bars 101. In some embodiments of the present disclosure, the arc frame bar 102A and the five straight frame bars 102B, 102C, 102D, 102E and 102F respectively have a diameter substantially ranging from 0.1 mm to 5 mm; and the connection bars 101 respectively have a diameter substantially ranging from 0.1 mm to 0.5 mm. The hexagon frame formed by the arc frame bar 102A and the five straight frame bars 102B, 102C, 102D, 102E and 102F has a surface area occupying about 3% to 5% area of the flat face 100A.

The connection bars 101 may be made of metal, semiconductor material, ceramic material, plastic material or the arbitrary combinations thereof. The materials used to compose the frame bars can be identical to or different from that used to compose the connection bars 101. For example, in the present embodiment, the 3D grid structure 100 can be fabricated by a metal melting process which comprises steps of guiding an energy beam (comprising the power sources, such as laser beam, electron beam, arc, plasma, electromagnetic conduction or the combination thereof) to smelt metal powder (comprising powder of titanium, gold, silver, iron or a combination thereof) by way of sintering, melting and solidification or a combination thereof, so as to form a porous array metal structure. The sintering process can be a selective laser sintering (SLS) process or a direct metal laser sintering (DMLS) process. The melting process can be a selective laser melting (SLM) process or an electron beam melting (EBM) process.

Figure 2:
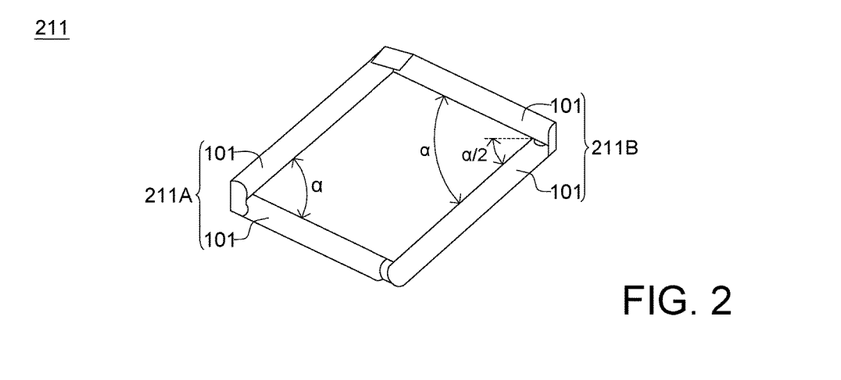
FIG. 2 is a perspective view illustrating a grid unit in accordance with one embodiment of the present disclosure.

In detail, the porous array metal structure formed by the metal melting process may shape as a 3D grid structure 100 composed by a plurality of grid units. FIG. 2 is a perspective view illustrating a grid unit 211 in accordance with one embodiment of the present disclosure. In the present embodiment, the grid unit 211 is a quadrilateral frame structure configured by at least four components of the connection bars 101 and the frame bars (not shown).

The quadrilateral frame structure of the grid unit 211 includes two sub-units 211A and 211B, and each of the sub-units 211A and 211B is either composed by two connected connection bars 101 or composed by one connection bar 101 and one frame bar connected with each other. Wherein the two connected connection bars 101 or the connected two of the connection bar 101 and the frame bar may form an angle α; and a half of the angle (α/2) substantially ranges from 45° to 75°. The angle α of the sub-units 211A and 211B can be adjusted to satisfy the rigidity (stiffness) requirement of the grid unit 211. In some embodiments of the present disclosure, the angle α of the sub-units 211A and 211B preferably is about 60°.

Figure 3:
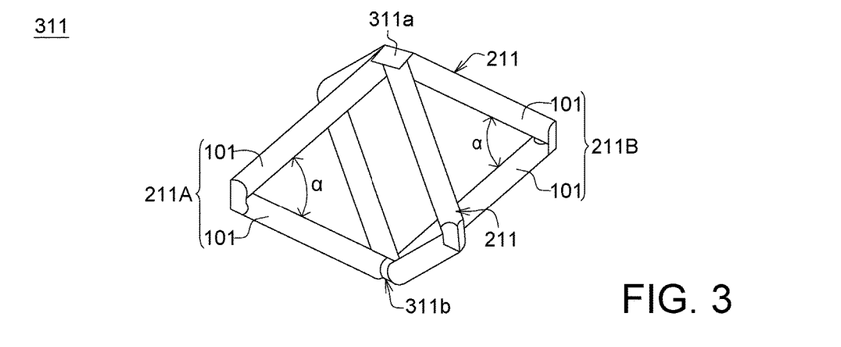
FIG. 3 is a perspective view illustrating a grid unit in accordance with another embodiment of the present disclosure.

FIG. 3 is a perspective view illustrating a grid unit 311 in accordance with another embodiment of the present disclosure. In the present embodiment, the grid unit 311 is an elongated square dipyramid (octahedron) configured by assembling two grid units 211 as depicted in FIG. 2, wherein the two rid units 211 are connected to each other at two vertices 311a and 311b of the elongated square dipyramid. In other words, the grid unit 311 is assembled by four sub-units, such as two sub-units 211A and two sub-units 211B, each of which has two ends respectively connected to the vertices 311a and 311b. The grid unit 311 has a volume substantially ranging from 1 mm$^3$ to 10 mm$^3$; the 3D grid structure 100 is composed by a plurality of identical grid units 311; and the 3D grid structure 100 has a total porosity substantially ranging from 60% to 80%.

Figure 4:
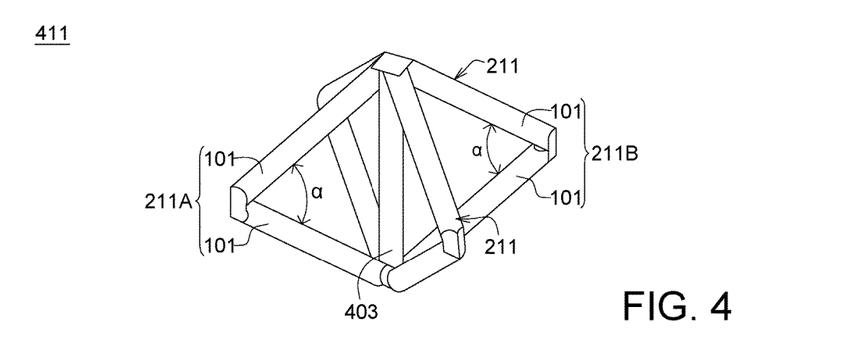
FIG. 4 is a perspective view illustrating a grid unit in accordance with yet another embodiment of the present disclosure.

FIG. 4 is a perspective view illustrating a grid unit 411 in accordance with yet another embodiment of the present disclosure. The structure of the grid unit 411 is similar to that of the grid unit 311 except that the grid unit 411 further includes a central rod 403 having two end respectively connected to the two ends of the four sub-units, such as two sub-units 211A and two sub-units 211B, assembled to form the grid unit 311 and serving as the opposite side of each sub-unit.

The central rod 403 can increase the rigidity (stiffness) of the grid unit 411 for resisting shearing stress. By comparison the rigidity (stiffness) to that of the grid units 211 and 311 respectively depicted in FIGS. 2 and 3, it can be observed that the grid unit 211 has a rigidity (stiffness) about 43.04 newton/meter (N/mm); the rigidity (stiffness) of the grid unit 311 is about 2145 N/mm; and the rigidity (stiffness) of the grid unit 411, in the present embodiment, can be increased up to 1054 N/mm, just because of the arrangement of the central rod 403.

It should be appreciated that the structure of the grid unit used to compose the 3D grid structure 100 is not limited to this regard. In some other embodiments, a single grid unit may include more sub-units, such as the sub-units 211A and 211B. And the grid structure 100 used to form the implant device 10 can be composed by different types of grid units.

Figure 5:
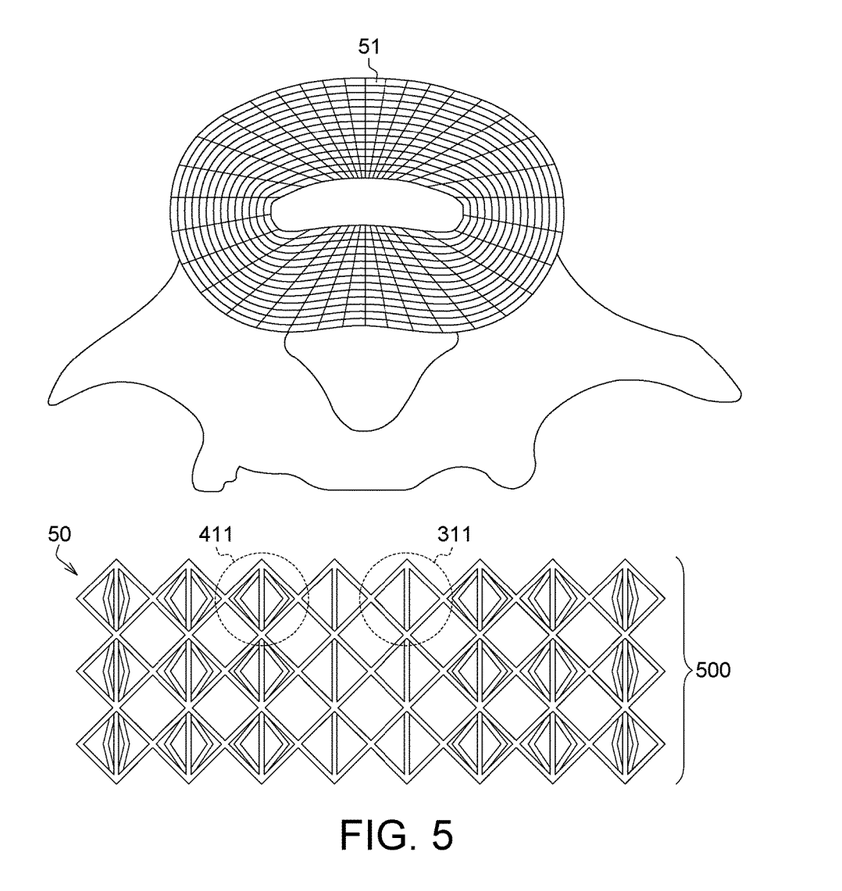
FIG. 5 is a partial perspective view illustrating an implant device for osseous integration in accordance with another embodiment of the present disclosure.

The implant device as discussed above can be applied to form orthopedic products, such as bone screws, spinal fixation device, inter-body fusion device, artificial disk, and artificial joints that can be implanted into bone tissues. FIG. 5 is a partial perspective view illustrating an implant device 50 for osseous integration in accordance with another embodiment of the present disclosure. In the present embodiment, the implant device 50 is an inter-body fusion device composed by different types of grid units, such as the grid units 211, 311 and 411 respectively depicted in FIGS. 2, 3 and 4, and the positions and arrangements of the grid units 211, 311 and 411 may be predetermined according to the bone mineral density and the stress parameters of the intervertebral disc 51 in which the implant device 50 is implanted. However, the applications of the implant device 50 are not limited as this regard.

In order to enhance the rigidity (stiffness) for resisting shearing stress, the implant device for osseous may further include at least one inner frame bar. Referring to FIG. 1A again, the implant device 10 for osseous integration further includes an inner frame 105 composed by four inner frame bars 104A, 104B, 104C and 104D connected with each other and disposed on the top flat face 100A of the 3D grid structure 100. Wherein each of the plurality of inner frame bars 104A, 104B, 104C and 104D connects to a connection bars 101 and has a diameter substantially greater than that of these connection bars 101.

Figure 6:
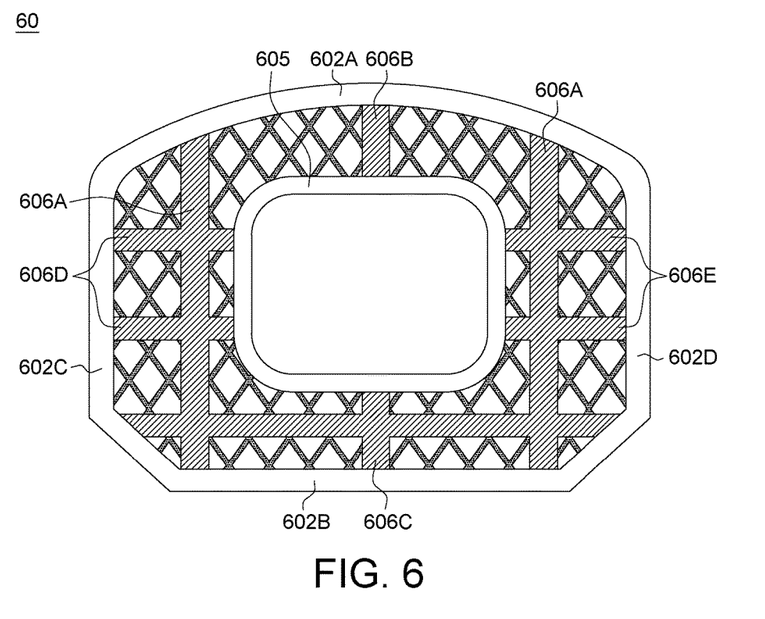
FIG. 6 is a top view illustrating an implant device for osseous integration in accordance with yet another embodiment of the present disclosure.

The implant device for osseous integration may further include a plurality reinforcing bars. FIG. 6 is a top view illustrating an implant device 60 for osseous integration in accordance with yet another embodiment of the present disclosure. The structure of the implant device 60 is similar to that of the implant device 10 except that the implant device 60 further includes a plurality reinforcing bars 606A, 606B, 606C, 606D and 606E. Wherein, the reinforcing bars 606A connects a frame bar 602A with another frame bar 602B; the reinforcing bars 606B connects the frame bar 602A with a the inner frame 605; the reinforcing bars 606C connects a frame bar 602B with a the inner frame 605; the reinforcing bars 606D connects a frame bar 602C with a the inner frame 605; and the reinforcing bars 606E connects a frame bar 602D with a the inner frame 605. Each of the reinforcing bars 606A, 606B, 606C, 606D and 606E connects at least two connection bars 101 and has a diameter substantially greater than that of these connection bars 101.

Figure 7A:
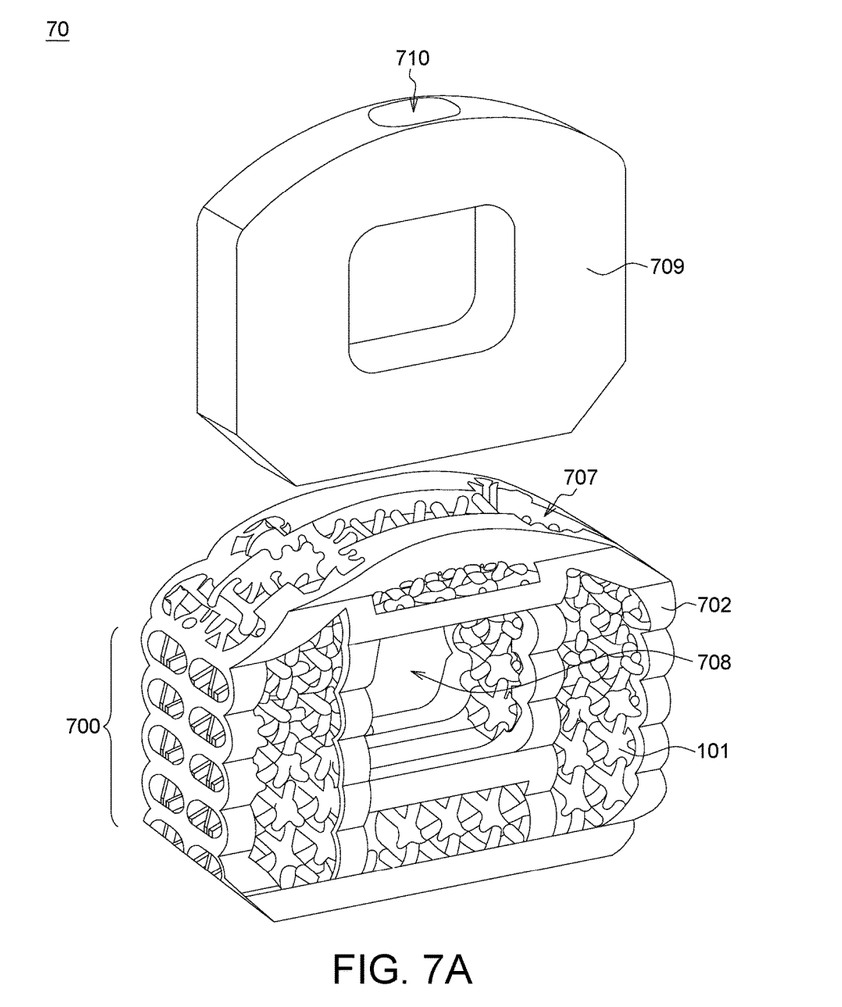
FIG. 7A is an exploded view illustrating an implant device for osseous integration in accordance with yet another embodiment of the present disclosure.
Figure 7B:
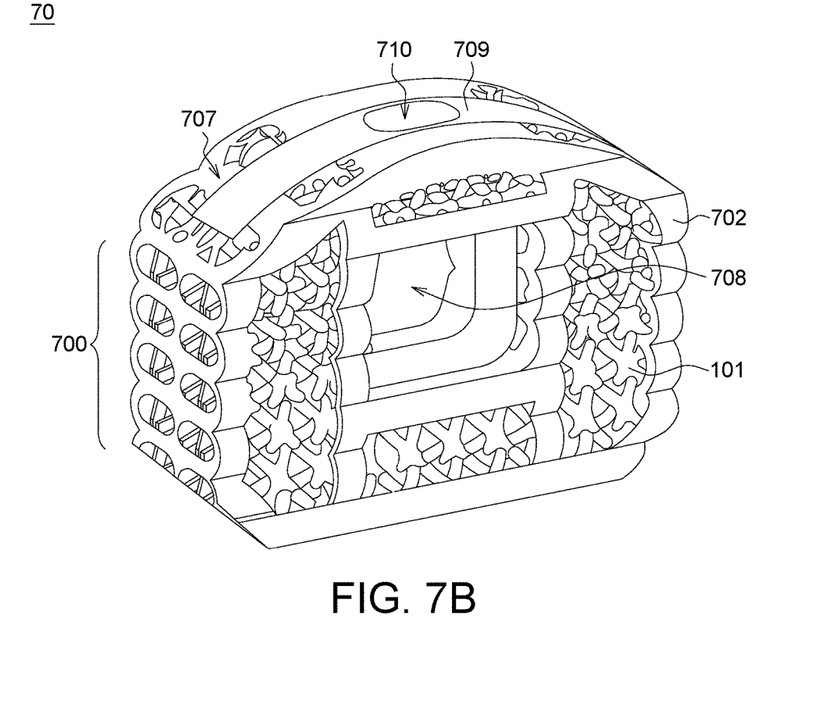
FIG. 7B is a perspective view illustrating the assembled structure of the implant device for osseous integration depicted in FIG. 7A.

In addition, FIG. 7A is an exploded view illustrating an implant device 70 for osseous integration in accordance with yet another embodiment of the present disclosure; and FIG. 7B is a perspective view illustrating the assembled structure of the implant device 70 for osseous integration depicted in FIG. 7A. One of the frame bars 702 may be designed as having a cross-section shaped as a continuous waving line or a continuous curve line; and the implant device 70 may further included a receiving opening 707 formed on a surface defined by the frame bars 702 and a receiving space 708 extending into the 3D grid structure 700 from the receiving opening 707.

In the present embodiment, the implant device 70 further includes a polymer body 709 passing through the receiving opening 707 and contained in the receiving space 708 to form a frictional interface having a contact area directly in contact with the 3D grid structure 700. Wherein the ratio of the contact area to an overlapping area formed between the 3D grid structure and the polymer body substantially ranges from 3% to 5%.

In detail, the receiving space 708 is defined by a plurality of connection bars 101 involved in the 3D grid structure. Each of the connection bars 101 used to define the receiving space 708 may have one end either connected with the other connection bards 101 to form a plurality of lumps, barb protrusions or serrated protrusions or singly suspended around the receiving space 708 and directly in contact with the polymer body 709 to form the contact area, while the polymer body 709 is contained in the receiving space 708 through the receiving opening 707. The polymer body 709 may be secured firmly in the 3D grid structure 700 by the fraction force formed between the polymer body 709 and the lumps, barb protrusions, serrated protrusions or the suspended end of the connection bards 101.

In some other embodiments of the present disclosure, after the polymer body 709 is secured in the receiving space 708, an additional metal melting process may be performed to form at least one additional connection bars or reinforce frame bars (not shown) to seal the receiving opening 707 and enclose the polymer body 709 in the 3D grid structure 700.

In some embodiments of the present disclosure, the polymer body 709 may be formed by performing injection, pultrusion, membrane pressing, thermal pressing, blow molding, molding, filament winding, prepreg material laminating, transferring, foaming, casting, or lamination on a thermoplastic plastic, such as polyethylene (PE), ultra-high-molecular-weight polyethylene (UHMWPE), polypropylene (PP), polystyrene (PS), polymethyl methacrylate (PMMA), polyvinyl chloride (PVC), nylon (Nylon), polycarbonate (PC), polyurethane (PU), polytetrafluoroethylene (PTFE), polyethylene terephthalate (PET, PETE), or a thermosetting plastic, such as epoxy, phenolic, polyimide, melamine formaldehyde resin.

In the present embodiment, the polymer body 709 is formed of a polymer comprising polyether ether ketone (PEEK), carbon reinforced (PEEK), polyetherketoneketone (PEKK), polyaryletherketone (PAEK) or the arbitrary combinations thereof. The properties of the p polymer body 709 are similar to that of human bones. For example, the polymer body 709 preferably has an elastic modulus substantially ranging from 2 Gpa to 22 Gpa. However it should be noted that the material and way for fabricating the polymer body 709 of the present disclosure is not limited thereto, and any polymer material and method suitable for contacting biological tissues are within the spirit of the present disclosure.

Because the polymer body 709 and the human bones has similar elastic modulus, stress shielding effect occurs on the prior art medical material that is formed of one single material can be avoided. In addition, since the 3D grid structure 700 has superior biocompatibility for inducing tissue cells to grow there on, thus the 3D grid structure 700 can be tightly fused with the tissues in which it is implanted. Moreover, the polymer body 709 is securely enclosed in the one-piece 3D grid structure 700 reinforced by the frame bars 702 and inner frame 705, the problems of delamination and unwanted shift may be unlikely to occur on the implanted device 70 due to the sudden impact resulted from the surgical operation or the prolonged extrusion stress provided by the peripheral cartilage or bone tissues. As a result, the problems encountered in generally known technology can be resolved.

In order to aid the physicians performing the implant surgery, in some embodiments of the present disclosure, the polymer body 709 may further include a working opening 710 aligning the receiving opening 707 and allowing a surgical equipment (not shown) engaged therewith to aid the physicians performing the implant surgery of the implant device 70.

Figure 8A:
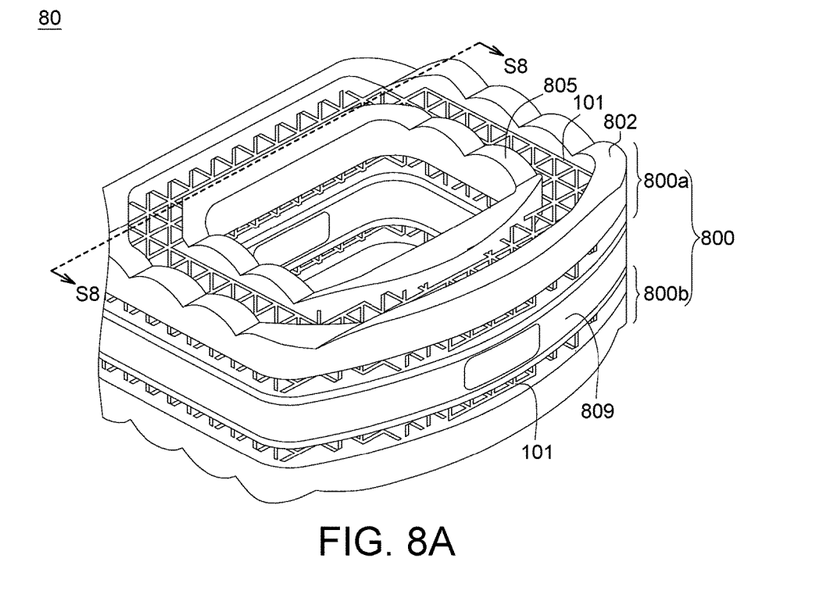
FIG. 8A is a perspective view illustrating an implant device for osseous integration in accordance with yet another embodiment of the present disclosure.
Figure 8B:
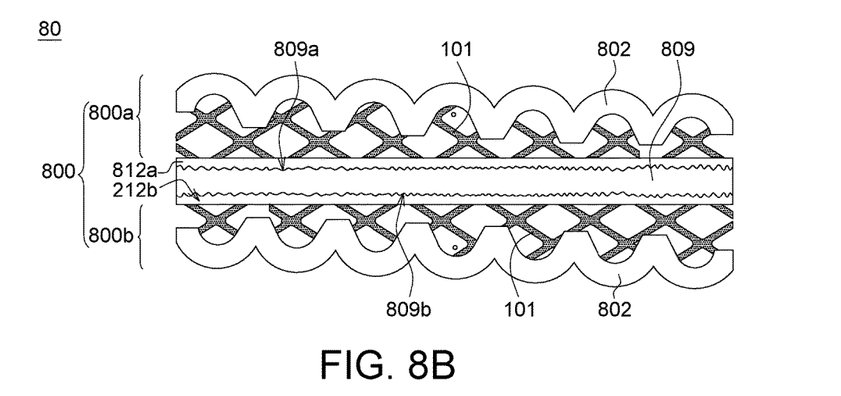
FIG. 8B is a cross-sectional view of the implant device for osseous integration taken along the section line S8 depicted in FIG. 8A.

FIG. 8A is a perspective view illustrating an implant device 80 for osseous integration in accordance with yet another embodiment of the present disclosure; and FIG. 8B is a cross-sectional view of the implant device 80 for osseous integration taken along the section line S8 depicted in FIG. 8A. The structure of the implant device 80 is similar to that of the implant device 70 except the way of engagement between the polymer body 809 and the 3D grid structure 800 in the implant device 80 is different from that of the implant device 70.

In the present embodiment, the 3D grid structure 800 of the implant device 80 is divided into two portions; one is the upper portion 800A, the other is bottom portion 800B. The polymer body 809 is connected to the connection bars 101 used to configure the upper portion 800A and the bottom portion 800B of the 3D grid structure 800 through two metal interface layers 812a and 812b, respectively. Each of the metal interface layers 812a and 812b has a connecting area directly in contact with the 3D grid structure 800, wherein the ratio of the connecting area to an overlapping area formed between the metal interface layer 812a (812b) and the upper portion 800A (bottom portion 800B) of 3D grid structure 800 substantially ranging from 3% to 5%. The bonding force between the metal interface layer 812a (812b) and the upper portion 800A (bottom portion 800B) of the 3D grid structure 800 can be enforced by increase the connecting area between metal interface layer 812a (812b) and the connection bars 101 of the upper portion 800A (bottom portion 800B) of the 3D grid structure 800.

In some embodiments of the present disclosure, the method for connecting the polymer body 809 with 3D grid structure 800 includes steps as follows: A surface roughening process is performed by way of CNC processing, laser surface treatment, plasma surface treatment, etching or a combination thereof to form a plurality of openings or grooves extending into a upper surface 809a and a bottom surface 809b of the polymer body 809 respectively, wherein each recess has an aspect ratio (depth to width) substantially ranging from 1 μm to 4000 μm.

A deposition process, such as (but is not limited to) physical vapor deposition (PVD), chemical vapor deposition (CVD), arc ion plating (AIP), sputtering deposition, arc spraying), flame spray, electroplating, powder plasma spray, electroless plating, powder plasma spraying, laser powder deposition, casting, curing colloidal solution or a combination thereof, is then performed to form interface layers 812a and 812b are respectively covering on the upper surface 809a and the bottom surface 809b of the polymer body 809 and filling into the recesses. In some embodiments of the present disclosure, the interface layers 812a and 812b are metal coating films conformally formed on and in contact with the upper surface 809a and the bottom surface 809b of the polymer body 809 respectively. The metal coating films can be made of titanium (Ti), titanium alloy (Ti-6Al-4V), cobalt-chromium alloy (Co—Cr), stainless steel (SUS 316L), gold (Au), or the arbitrary combinations thereof. The thickness of the interface layers 812a and 812b respectively measured from the upper surface 809a and the bottom surface 809b of the polymer body 809 may substantially range from 30 μm to 500 μm. The thickness of the upper portion 800A and the bottom portion 800B of the 3D grid structure 800 may respectively range from 10 μm to 5000 μm.

Next, the upper portion 800A and the bottom portion 800B of the 3D grid structure 800 are respectively formed on the surfaces of the interface layers 812a and 812b separated from the polymer body 809. In the present embodiment, since the structure, materials and method for forming the upper portion 800A and the bottom portion 800B of the 3D grid structure 800 are exactly identical to that for forming the 3D grid structure 100, thus the similarities are not redundantly repeated herein.

Because the polymer body 809 and the human bones has similar elastic modulus, stress shielding effect occurs on the prior art medical material that is formed of one single material can be avoided. In addition, since the 3D grid structure 800 has superior biocompatibility for inducing tissue cells to grow there on, thus the 3D grid structure 800 can be tightly fused with the tissues in which it is implanted. Moreover, the interface layers 812a and 812b can serve as a thermal diffusion buffer to avoid the thermal stress concentrated in the subsequent processes from penetrating and damaging the polymer body 809 and can disperse mechanical stress exerted on the polymer body 809 to avoid interface layers 812a and 812b from peeling off the polymer body 809 and the 3D grid structure 800 reinforced by the frame bars 802 and inner frame 805, the problems of delamination and unwanted shift may be unlikely to occur on the implanted device 80 due to the sudden impact resulted from the surgical operation or the prolonged extrusion stress provided by the peripheral cartilage or bone tissues. As a result, the problems encountered in generally known technology can be resolved.

According to the aforementioned embodiments, an implant device for osseous integration is disclosed. The implant device for osseous integration includes a plurality of connection bars used for forming a 3D grid structure and at least one frame bar used to define at least one edge of the 3D grid structure. Because the frame bar has a diameter substantially greater than that of these connection bars can provide the 3D grid structure more rigid structure for resisting the sudden impact resulted from the surgical operation or the prolonged extrusion stress provided by the peripheral cartilage or bone tissues, so as to avoid delamination and unwanted shift occurring on the implanted device.

It will be apparent to those skilled in the art that various modifications and variations can be made to the disclosed embodiments. It is intended that the specification and examples be considered as exemplary only, with a true scope of the invention being indicated by the following claims and their equivalents.

What is claimed is:

1. An implant device for osseous integration, comprising:
a plurality of connection bars, connected with each other to form a three-dimensional (3D) grid structure; and
at least one frame bar, connected with at least two of the connection bars to define at least one edge of the 3D grid structure;
wherein, the frame bar has a diameter greater than that of the connection bars; the 3D grid structure comprises at least one grid unit which is an elongated square dipyramid (octahedron) assembled by four sub-units and having a volume ranging from 1mm³ to 10 mm³.

2. The implant device for osseous integration according to claim 1, wherein the grid unit is configured by at least four components of the connection bars.

3. The implant device for osseous integration according to claim 1, wherein each of the sub-units is either composed by two of the connected connection bars or composed by one of the connection bars and one of the frame bars which are connected to each other, wherein the two connected connection bars or the connected two of the connection bar and the frame bar form an angle; and a half of the angle ranges from 45° to 75°.

4. The implant device for osseous integration according to claim 3, wherein the grid unit further comprises a central rod serving as the opposite side of each sub-unit.

5. The implant device for osseous integration according to claim 1, wherein the 3D grid structure has a total porosity ranging from 60% to 80%.

6. The implant device for osseous integration according to claim 1, further comprising at least one inner frame bar used to define an inner frame disposed on a flat face of the 3D grid structure.

7. The implant device for osseous integration according to claim 1, further comprising a polymer body contained within the 3D grid structure to form a frictional interface having a contact area directly in contact with the 3D grid structure; wherein a ratio of the contact area to an overlapping area formed between the 3D grid structure and the polymer body ranges from 3% to 5%.

8. The implant device for osseous integration according to claim 7, further comprising:
a receiving opening, formed on a surface of the 3D grid structure; and
a receiving space, extending into the 3D grid structure from the receiving opening and used to contain the polymer body.

9. The implant device for osseous integration according to claim 7, wherein the polymer body further comprises a working opening aligning the receiving opening and allowing a surgical equipment engaged therewith to aid a physician performing an implant surgery of the implant device.

10. The implant device for osseous integration according to claim 7, wherein each of the connection bars used to define the receiving space has one end protruding around the receiving space and directly in contact with the polymer body to form a frictional interface.

11. The implant device for osseous integration according to claim 6, further comprising at least one reinforcing bar having a diameter greater than that of the connection bars, disposed on the surface of the of the 3D grid structure, and used to either connect with two of the at least one frame bar or connected the frame bar with the inner frame bar.

12. The implant device for osseous integration according to claim 1, further comprising a polymer body, connected to the 3D grid structure through a metal interface layer having a connecting area directly in contact with the 3D grid structure; wherein a ratio of the connecting area to an overlapping area formed between the metal interface layer and the 3D grid structure ranging from 3% to 5%.

13. The implant device for osseous integration according to claim 12, wherein the metal interface layer is a metal coating layer conformally formed on a surface of the polymer body and made of titanium (Ti), titanium alloy (Ti-6Al-4V), cobalt-chromium alloy (Co—Cr), stainless steel (SUS 316L), gold (Au), or arbitrary combinations thereof.

14. The implant device for osseous integration according to claim 12, wherein the polymer body comprises polyether ether ketone (PEEK), carbon reinforced (PEEK), polyetherketoneketone (PEKK), polyaryletherketone (PAEK) or arbitrary combinations thereof.

15. The implant device for osseous integration according to claim 12, wherein the interface layer has a thickness ranging from 30 μm to 500 μm; and the 3D grid structure has a thickness ranging from 10 μm to 5000 μm.

16. The implant device for osseous integration according to claim 1, wherein the frame bar is disposed on a flat surface of the 3D grid structure and has a surface area occupying about 3% to 5% area of the flat face.

17. The implant device for osseous integration according to claim 1, wherein the 3D grid structure comprises Ti.

18. The implant device for osseous integration according to claim 1, wherein the implant device for osseous integration is a bone screw, a spinal fixation device, an inter-body fusion device, an artificial disk, or an artificial joint.

19. The implant device for osseous integration according to claim 1, wherein the frame bars have a cross-section shaped as a continuous waving line or a continuous curve line.

* * * * *